Figure 2:
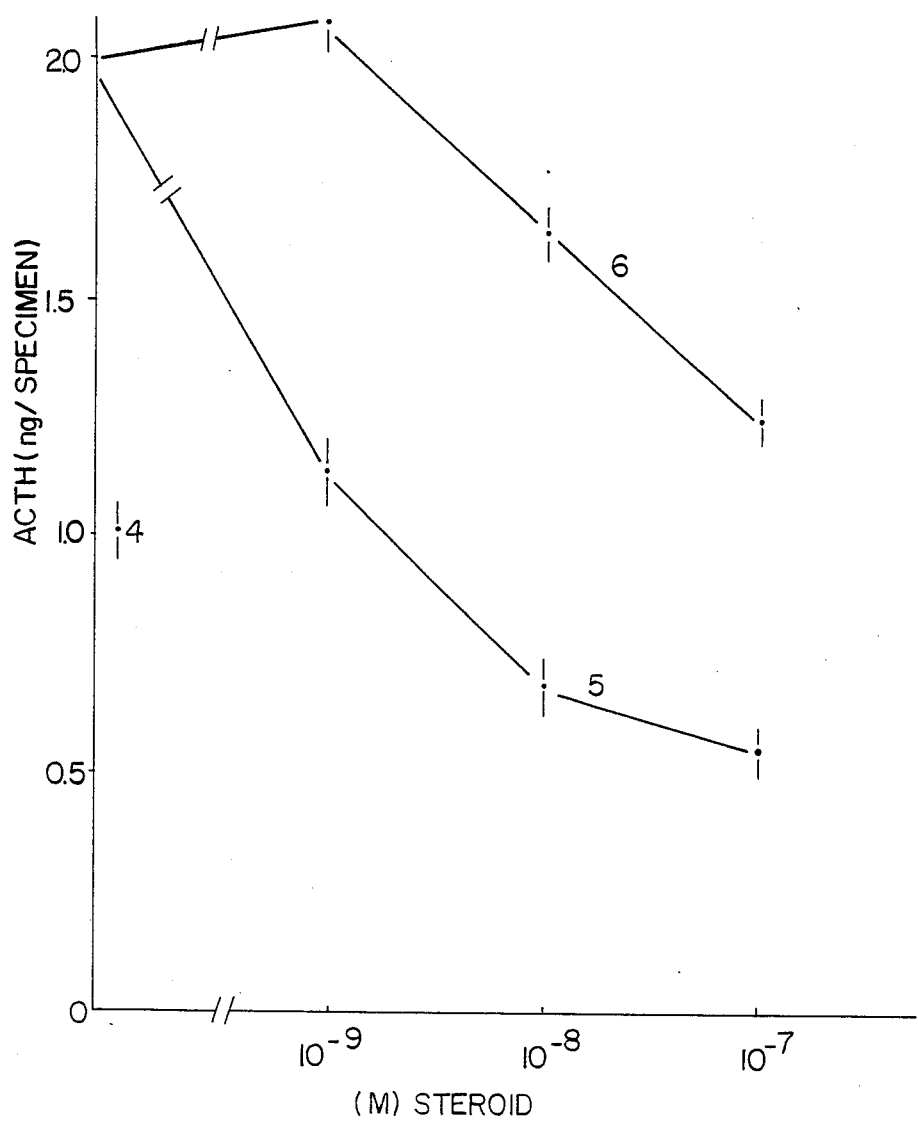

United States Patent [19]

Milioni et al.

[11] Patent Number: 4,913,852
[45] Date of Patent: Apr. 3, 1990

[54] COMPOUNDS OBTAINED FROM THE ASSOCIATIVE SYNTHESIS OF SULFUR-CONTAINING OR SULFUR-FREE AMINO ACIDS WITH PREGNANE DERIVATIVES

[76] Inventors: Catherine Milioni, 84, Rue 17 Noemvriou; Constantin Efthyimiopoulos, 74, rue 17 Noemvriou, both of 16341 Ilioupoli, Greece; Bernard Koch, 24a, rue de Lièpvre, 67100 Strasbourg, France; Louis Jung; Jean Jung, both of 205, route d'Oberhausbergen, 67200 Strasbourg, France

[21] Appl. No.: 166,122
[22] PCT Filed: Jun. 24, 1987
[86] PCT No.: PCT/FR87/00244
§ 371 Date: Feb. 24, 1988
§ 102(e) Date: Feb. 24, 1988
[87] PCT Pub. No.: WO88/00202
PCT Pub. Date: Jan. 14, 1988

[30] Foreign Application Priority Data
Jun. 24, 1986 [FR] France .................. 86 09246

[51] Int. Cl.$^4$ .................. C07S 9/00; A61K 31/56
[52] U.S. Cl. .................. 514/179; 514/174; 514/176; 514/180; 514/181; 540/67; 540/108; 540/111; 552/523; 552/529; 552/565; 552/566; 552/564; 552/580; 552/581; 552/572; 552/573; 552/574; 552/575; 552/588; 552/589; 552/590; 552/594; 552/595; 552/596; 552/597; 552/598; 552/601; 552/602; 552/604; 552/605; 552/607; 552/608
[58] Field of Search .................. 514/178, 180; 260/397.2

[56] References Cited
FOREIGN PATENT DOCUMENTS
962797 7/1964 United Kingdom .
1324911 7/1973 United Kingdom .

OTHER PUBLICATIONS
"Solution Kinetics of a Water-Soluble Hydrocortisone Prodrug: Hydrocortisone-21-Lysinate", *Journal of Pharmaceutical Sciences*, vol. 74, No. 1, By K. Johnson et al., Jan. 1985, pp. 87–89.

Primary Examiner—Douglas W. Robinson
Assistant Examiner—Raymond J. Henley, III
Attorney, Agent, or Firm—Young & Thompson

[57] ABSTRACT

Compounds obtained from the associative synthesis of sulfur-containing or sulfur-free amino acids with derivatives of Δ-4-pregnene-3,20-dione or with derivatives of Δ-1,4-pregnadiene-3,20-dione of the general formulas (I), (II) and (III), having glucocorticoidal and anti-inflammatory properties have been prepared and tested. Pharmaceutical compositions, medicaments containing them as well as their applications are claimed, particularly in the cutaneous and ophthalmic fields.

(Abstract continued on next page.)

-continued
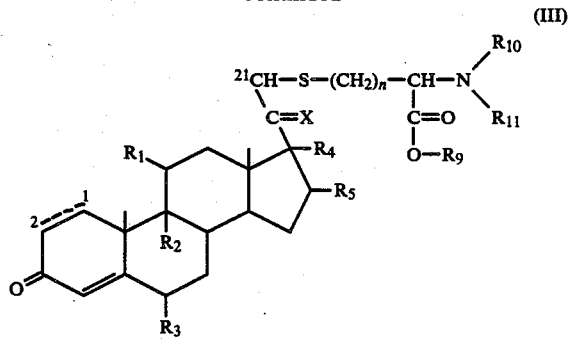
20 Claims, 2 Drawing Sheets

FIG.I
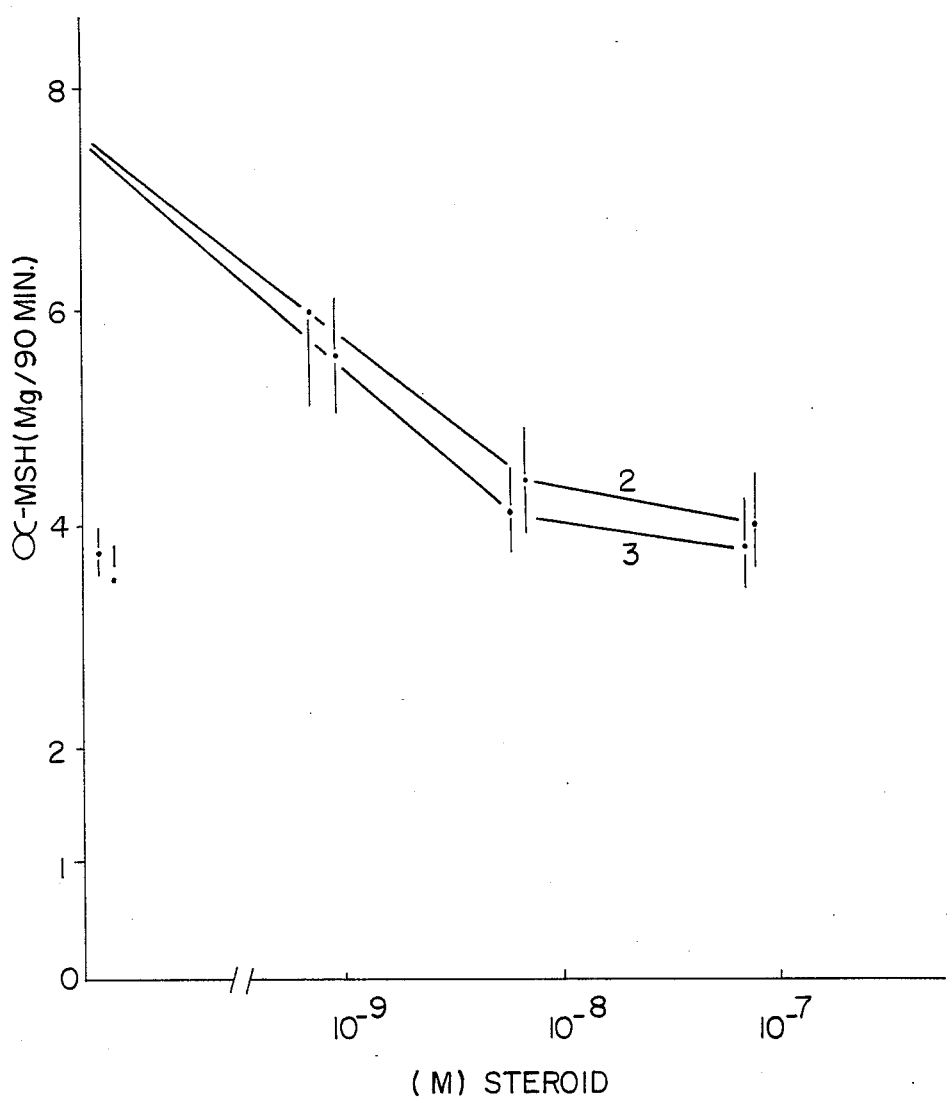

COMPOUNDS OBTAINED FROM THE ASSOCIATIVE SYNTHESIS OF SULFUR-CONTAINING OR SULFUR-FREE AMINO ACIDS WITH PREGNANE DERIVATIVES

The invention has as an object novel compounds obtained from the associative synthesis of sulfur-containing or sulfur-free amino acids with derivatives of Δ-4-pregnene-3,20-dione or with derivatives of Δ-1,4-pregnadiene-3,20-dione, as well as their addition salts with mineral or organic acids in the presence of the amino group or their mineral salts in the presence of the carboxylic group, processes for their preparation, their pharmacological activity and pharmaceutical compositions containing them.

At present, anti-inflammatory steroids having hydrosolubility have already been described, especially as regards their use by injectable means. To this end, synthesis of esters at the 21 and/or 17 position of steroids with polybasic acids or amino acids has already been described.

On the other hand, anti-inflammatory steroids obtained from the associative synthesis between amino acids and steroids having an ester function at the 21 position and sulfur-containing at the level of the side chain, but not having a salifiable free amino group have also already been described.

The present invention concerns anti-inflammatory steroid compounds resulting from an associative synthesis between steroid and amino acids and having a reservoir effect associated with a cutaneous tropism where a hydrosoluble group in the form of a mineral or organic salt is favorable.

To obtain this conjoint double activity, the claimed novel structures respond to the three general formulas I, II and III, and have:

Either an ester bond at position 21 but comprising a sulfur-containing amino acid structure with a free amino group (general formula I).

Or an amino group at position 21 obtained from sulfur-containing or sulfur-free amino acid (formula II), Or a sulfur-containing group at position 21 and a terminal amino acid structure (formula III),

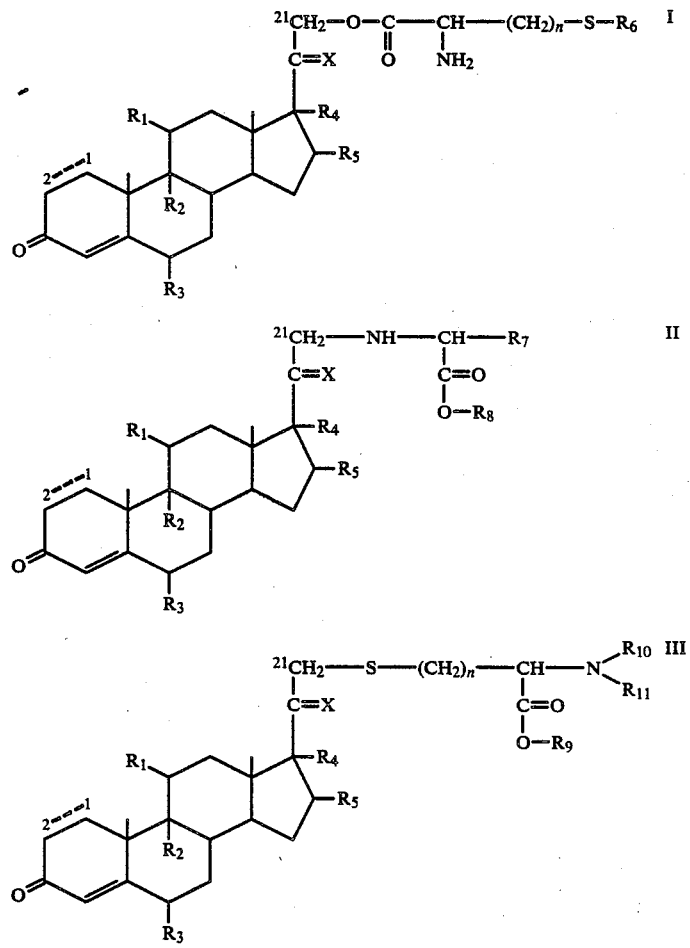

in which:
for the three general formulas I, II, and III the $C_1$–$C_2$ bond may be a saturated bond (hydrocortisone derivatives for example), or may be an ethylenic bond (dexamethasone derivatives for example);

$R_1$ represents oxygen, sulfur, or chlorine or hydroxy;

$R_2$ and/or $R_3$ represent hydrogen, fluorine, chlorine or methyl;

$R_4$ and/or $R_5$ represent hydrogen, hydroxy, methyl or ethyl; $R_5$ may also be methylene;

$R_4$ and $R_5$ may form a heterocycle of the type —O—CH(Y)—O— or —O—C(Y)$_2$—O—, Y being hydrogen or straight or branched chain alkyl having preferably 1 to 4 carbon atoms;

X represents oxygen or sulfur;

for formula I n is 1 or 2;

$R_6$ may represent methyl, an arylalkyl group, or any other group used for protecting the thiol function;

$R_6$ may correspond to the entire structure I giving a duplication of formula I with formation of a disulfur bridge;

for formula II $R_7$ represents hydrogen obtained from glycine, or a linear alkyl group, especially methyl obtained from alanine, or a branched chain alkyl group, obtained from valine, leucine, isoleucine, or a linear hydroxyalkyl group, obtained from serine, threonine, or a thioalkyl group obtained from methionine, or a thioalkyl group obtained from cysteine, or an arylalkyl group for example either benzyl obtained from phenylalanine, or hydroxybenzyl obtained from tyrosine, or indolylalkyl obtained from tryptophan, or imidazolylalkyl obtained from histidine, or an amidoalkyl group obtained from asparagine, glutamine, or a carboxylic alkyl group in free form or salified with sodium, obtained for example from aspartic acid, glutamic acid or cyclicized in the form of pyroglutaminic acid, or an alkyl amino group obtained from lysine, or a guanidinoalkyl group obtained from arginine, or also a dithiodimethyl group obtained from cystine, symmetrically fixing two glucocorticoids;

the NH group may form with $R_7$ a nitrogen-containing heterocycle of the pyrrolidine type obtained from proline;

the various amino acids named may be replaced by their upper homologs;

$R_8$ may be hydrogen or a corresponding salt such as sodium, potassium, calcium;

$R_8$ may also be a straight, or branched chain alkyl group preferably having 1 to 4 carbon atoms, or an arylalkyl group of the benzyl or heterocyclic type;

for formula III n varies from 1 to 6, but it is preferred that $n=1$ obtained from cysteine, or $n=2$ obtained from homocysteine;

$R_9$ may assume the various structures recited for $R_8$;

$R_{10}$ and/or $R_{11}$ may represent hydrogen, or a straight or branched chain alkyl group preferably having 1 to 3 carbon atoms, in the form of an ammonium or amino-containing structure;

$R_{10}$ or $R_{11}$ may also be a structure —CO—Z—, Z being a straight or branched chain alkyl group, or arylalkyl.

The invention also has an object processes for preparing derivatives as defined by formulas I, II and III above.

For the derivatives of formula I, the process consists of successive transformations of the steroid to mesylate then to an iodine-containing derivative, this latter reacting with the carboxylic function of an amino acid whose amine function is protected by tert-butyloxycarbonyl. Thereafter, the protective group of the amine function is eliminated. The steroid may be hydrocortisone, or dexamethasone or any other glucocorticoid steroid having the —CO—$CH_2OH$ chain, the amino acid is especially cystine, methionine, or also cysteine of which the thiol function is protected.

For derivatives of formula II, the process consists of successive transformations of the steroid to mesylate then to an iodine-containing derivative, this latter reacting with the amino function of an amino acid whose carboxylic function is protected by various ester groupings. The reaction may be effected in the same conditions, starting from the 21-mesylate of the steroid. The steroid may be hydrocortisone or dexamethasone or any other glucocorticoid steroid having a CO—$CH_2OH$ chain, the amino acid may be especially cystine, methionine, glutamic acid, or also pyroglutamic acid.

For derivatives of formula III, the process consists of transformation of the steroid to mesylate which reacts with an amino acid having a free SH thiol group, such as for example cysteine or homocysteine.

The invention also has as an object the preparation of compounds defined by formulas I, II and III, in the form of addition salts with mineral or organic acids in the presence of the amino group, or their mineral salts in the presence of the carboxylic group, especially in the form of sodium, potassium or calcium carboxylates.

The compounds of formula I, II or III are characterized in that they advantageously represent one of the following compounds:

ester between hydrocortisone and cystine (formula I);

ester between dexamethasone and cystine (formula I);

ester between hydrocortisone and methionine (formula I);

ester between dexamethasone and methionine (formula I);

amine at position $C_{21}$ between hydrocortisone and methionine (formula II);

amine at position $C_{21}$ between dexamethasone and methionine (formula II);

amine at position $C_{21}$ between hydrocortisone and cystine (formula II);

amine at position $C_{21}$ between dexamethasone and cystine (formula II);

thiol ether at position $C_{21}$ between hydrocortisone and cysteine (formula III);

thiol ether at position $C_{21}$ between dexamethasone and cysteine (formula III).

The invention will now be described in greater detail in the examples set forth hereinafter in a non-limiting manner, among which:

EXAMPLE 1

Synthesis of diesters of cystine from anti-inflammatory steroids. (Example corresponding to compounds of general formula I)

The steroid is transformed to 21-mesylate by the action of methane sulfonic acid chloride in pyridine. The synthesized derivative was transformed by the action of sodium iodide in acetone, to an iodine-containing derivative. The diester was formed by the reaction of the iodine-containing derivative with cystine, the amino function of which was first protected by tert-butyloxycarbonyl, in DMF and in the presence of triethylamine. The final product with the free amino group was obtained in the form of addition salt with hydrobromic acid, after having eliminated the tert-butyloxycarbonyl group through the action of an acetic acid/hydrobromic acid mixture.

The final product was characterized on chromatographic plate by specific coloration (red on yellow base) of disulfides, after atomization with a solution of sodium nitroprusside, followed by atomization with a solution of sodium cyanide. The characterization was completed by infrared spectral analyses and nuclear magnetic resonance. The structure was verified by determination of the molecular mass in mass spectrometry.

EXAMPLE 2

Synthesis of amino-containing and sulfur-containing anti-inflammatory steroids (compounds of general formula II)

The iodine-containing derivative of the steroid reacts in DMF with methionine, first esterified, to form the amino-containing and sulfur-containing steroid. The desired compound is finally obtained in hydrochloride form after appropriate treatment of the reaction medium (gaseous hydrochloric acid in methanol, then addition of ethyl ether)

The reaction could be effected under the same conditions, starting with the 21-mesylate of the steroid.

For compounds of general formula III, the preparation process is identical to that for compounds of general formula II in reacting cysteine with the 21-mesylate of hydrocortisone or dexamethasone.

Methods of preparation of the various derivatives are as follows:

The preparation of the synthetic intermediates is described for dexamethasone, which could be replaced by any glucocorticoid steroid having a —CO—CH$_2$OH chain at position 21.

21-methane sulfonate of dexamethasone 500 mg (1.3 mmol) dexamethasone is dissolved in 8 ml anhydrous pyridine and the solution is agitated at 0° C. 0.4 ml methane sulfonic acid chloride is added. This solution is agitated at 0° C. for one hour. 0.2 ml methane sulfonic acid chloride is added to the solution and agitation is continued for 30 additional minutes. The solution is placed in cold water under strong agitation. A white precipitate forms which is filtered and carefully washed with water, then dried over P$_2$O$_5$ in an evacuated desiccator.

M.P.=246° C.
Yield: 85%.

21-iodo of dexamethasone 520 mg (1.1 mmol) 21-methanesulfonate of dexamethasone is dissolved in 10 ml anhydrous acetone, then 600 mg anhydrous sodium iodide is added. The mixture is refluxed for 2 hours, then after elimination of excess acetone, the residue is added to water under strong agitation. A pale yellow precipitate forms which is filtered and washed with water, then dried over P$_2$O$_5$.

M.P.: 210° C.
Yield: 75%.

Di-(21-desoxydexamethasone) ester cystine dihydrobromate 1 g (3.4 m mol) N,N'-di-t-butyloxycarbonyl cystine and 5.5 ml triethylamine are added to 20 ml anhydrous DMF. The solution is agitated for several minutes, then 3.01 g (6.3 mmol) of 21-iododexamethasone is added. After two hours of agitation at 40° C., the solution is added to 100 ml ethyl acetate. The organic phase is successively washed with water, a 5% NaHCO$_3$ solution, a 1% aqueous HCl solution, and finally with water. The organic phase is dried over MgSO$_4$ and evaporated to dryness.

The product was obtained in the form of an addition salt with hydrobromic acid, after having eliminated the tert-butyloxycarbonyl group by action of an acetic acid/hydrobromic acid mixture.

M.P.: 220° C.
Yield: 12% (after deprotection).

The same methods of operation were followed for synthesis of derivatives from hydrocortisone, as well as for derivatives of cystine with other protective groups for the amine function.

Methyl 21-N-(21-desoxyhydrocortisone)methionylate 0.45 g (2.2 mol) methionine methyl ester in hydrochloride form is dissolved in 30 ml anhydrous DMF. 4.76 ml triethylamine is added and the solution is agitated for several minutes. After addition of 1 g (2.28 mmol) 21-methane sulfonate of hydrocortisone, the reaction mixture is heated at 40° C. for two hours. The solution is added to 150 ml cold water and extracted three times with 100 ml AcOEt. The organic phase is washed with a saturated sodium chloride solution then dried over MgSO$_4$ and evaporated under vacuum. The residue is dissolved in methanol and transformed to the hydrochloride by the action of gaseous hydrochloric acid. After addition of anhydrous ether a white precipitate forms which is filtered, then dried over P$_2$O$_5$.

M.P.: 238° C., dec.
Yield: 60%.

So as to illustrate the invention in a non-limiting manner, results of the pharmacological study which was carried out in relation to these substances are shown below; and are explained with reference to the accompanying schematic drawings in which:

FIG. 1 represents the effect of the synthetic derivatives on secretion of 1'α-MSH, induced by CRF, by corticotropic cells in culture (curve 1: without CRF, curve 2: dexamethasone, curve 3: aminated and sulfur-containing hydrocortisone, n=15);

FIG. 2 represents the effect of the synthetic derivatives on secretion of ACTH induced by CRF, by corticotropic cells in culture (curve 4: without CRF, curve 5: dexamethasone, curve 6: sulfur-containing dexamethasone, n=15).

It was found that the compounds according to the invention may be applied in the manufacture of a medicament intended for therapeutic use as an anti-inflammatory agent, particularly for cutaneous and ophthalmic applications.

In a first instance, there was studied the effects of the synthesized molecules on secretion of 1'α-MSH or ACTH, induced by CRF, by AtT-20 corticotropic tumor cells in culture.

The principle of this test rests on the capacity of corticotropic cells (derivatives from anterior hypophysis tumor) to secrete corticotropin (ACTH), 1'α-MSH (α-Melanocyte Stimulating Hormone) and other peptides with an activity that resembles that of endorphines.

This secretion is stimulated by the hypothalamus factor CRF (Corticotropin-Releasing Factor).

Decrease in scretion of 1'α-MSH or ACTH is thus indicative of glucocorticoid activity in the synthesized steroids. The quantity of 1'α-MSH or ACTH secreted was determined by radioimmunological methods (RIA).

The AtT-20 corticotropic tumor cells were incubated in a culture medium constituted of 90% DME (Dulbecco's modified Eagle's medium) and 10% serum (fetal bovine serum). Incubation is for 6 hours in the presence of steroids at a concentration of $10^{-9}$, $10^{-8}$ and $10^{-7}$M.

These cells are then washed and preincubated for 60 minutes in medium without serum.

After addition of CRF (10 nM) these cells were incubated for 90 minutes in the presence of steroids at the previously recited concentrations.

The effect of the synthesized molecules on secretion of 1'α-MSH or ACTH, induced by CRF, by AtT-20 corticotropic cells in culture, is represented in FIG. 1 and FIG. 2, respectively.

Incubation effected in the absence of steroids and CRF served for the control.

The glucocorticoid activity of aminated and sulfur-containing hydrocortisone (FIG. 1) is equivalent to that of dexamethasone.

Sulfur-containing dexamethasone is about ten times less active than dexamethasone (FIG. 2).

The results show that an amine function or a thio ether may replace the primary alcohol of the side chain of the anti-inflammatory steroid without causing a significant decrease in the glucocorticoid activity.

In a second instance, there was effected the study of the local anti-inflammatory activity of the derivatives synthesized according to the carrageenin abscess technique.

The carrageenin abscess technique consists of subcutaneously injecting a rat with a 2% carrageenin solution, which develops an inflammatory reaction characterized by formation of an abscess. Topical application of steroid reduces this inflammatory response, which is quantified by weighing the granuloma after dissection.

The novel compounds described are at least as active as hydrocortisone or dexamethasone taken as references.

Examples of pharmaceutical preparations including these novel compounds obtained from associative synthesis may be presented:

Collyrium:
Sulfur-containing and/or aminated steroid . . . 5 to 100 mg excipients: anhydrous monosodium phosphate, sodium hydrogenophosphate, sodium chloride, hydroxyethylcellulose, polysorbate 80, distilled water.

Cream:
Sulfur-containing and/or aminated steroid . . . 5 to 100 mg excipients: cetylstearic alcohol, PEG 1000 monocetylether, vaseline oil, vaseline, methyl and propyl parahydroxybenzoate, citric acid, sodium citrate, distilled water.

Ointment:
Sulfur-containing and/or aminated steroid . . . 5 to 100 mg excipients: polyethylene and paraffin oil Lotion:
Sulfur-containing and/or aminated steroid . . . 5 to 100 mg excipients: glycerine, isopropyl alcohol, polyvidone, excipient, citric acid, sodium citrate, distilled water.

The sulfur-containing steroids, by fixing to the keratin of the skin are active principals strongly fixed at the level of the epidermis (reservoir effect); their liberation is progressive and uniform only while under the influence of the cutaneous esterases.

The sulfur-containing and aminated steroids have a reservoir effect by fixing at the level of the epidermis and an increased activity.

What is claimed is:
1. A compound represented by one of the following formulae:

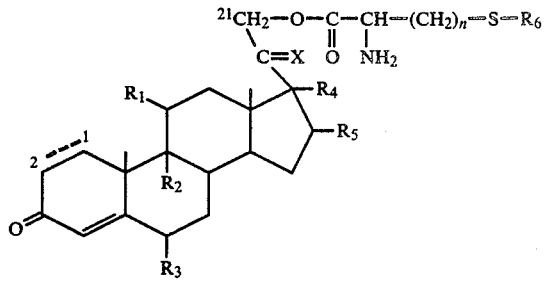

wherein n is 1 or 2;

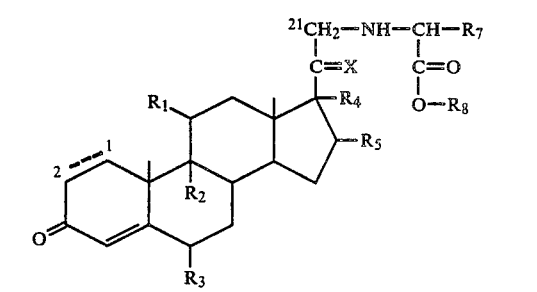

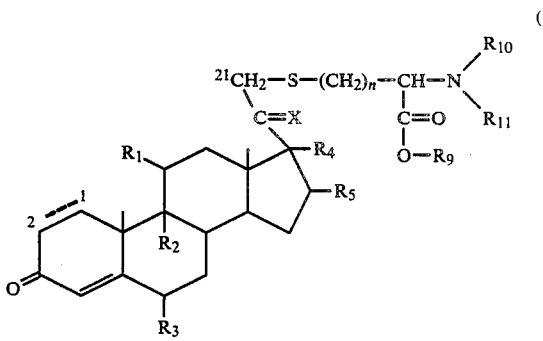

wherein n is from 1 to 6; and
wherein the $C_1$–$C_2$ bond may be a saturated or ethylenic bond;

$R_1$ is oxygen, sulfur, chlorine or hydroxy;
$R_2$ is hydrogen, fluorine, chlorine or methyl;
$R_3$ is hydrogen, fluorine, chlorine or methyl;
$R_4$ is hydrogen, hydroxy, methyl, or ethyl;
$R_5$ is hydrogen, hydroxy, methyl, ethyl or methylen
$R_4$ and $R_5$ may form a heterocycle of the ty]
—O—CH(Y)—O— or —O—C(Y)$_2$—O, where Y is hydrogen or a straight or branched chain alk group;
X is oxygen or sulfur;
$R_6$ is methyl, arylalkyl, or any other group whi protects the thiol function; $R_6$ may correspond formula (I) in its entirety with the formation of disulfur bridge;
$R_7$ is hydrogen, a linear alkyl group, a branched cha alkyl group, a linear hydroxy alkyl group, a thio: kyl group, an arylalkyl group, a hydroxybenz group, indolyalkyl, imidazolyalkyl, amidoalk: glutamine, a carboxylic alkyl group is free form salified by sodium, an alkyl amino group, a guanidinoalkyl group, a dithiodimethyl group;

the NH group in formula (II) may form with $R_7$ a nitrogen-containing heterocycle of the pyrrolidine type;

$R_8$ is hydrogen, a sodium salt, a potassium salt or calcium salt, a straight or branched chain alkyl group, a heterocyclic group, or an arylalkyl group;

$R_9$ is a straight or branched chain alkyl group, a heterocyclic group, or an arylalkyl group;

$R_{10}$ is hydrogen, a straight or branched chain alkyl group containing amino or ammonium;

$R_{11}$ is hydrogen, a straight or branched chain alkyl group containing amino or ammonium; and $R_{10}$ and $R_{11}$ may have the structure —CO—Z— wherein Z is a straight or branched chain alkyl group or an arylalkyl; and pharmaceutically acceptable salts thereof.

2. A compound according to claim 1, said compound being selected from the group consisting of compounds having an ester bond between hydrocortisone and cystine;
an ester bond between dexamethasone and cystine;
an ester bond between hydrocortisone and methionine;
an ester bond between dexamethasone and methionine;
an amine at position $C_{21}$ between hydrocortisone and methionine;
an amine at position $C_{21}$ between dexamethasone and methionine;
an amine at position $C_{21}$ between hydrocortisone and cystine;
an amine at position $C_{21}$ between dexamethasone and cystine;
a thiol ether at position $C_{21}$ between hydrocortisone and cysteine; and
a thiol ether at position $C_{21}$ between dexamethasone and cysteine.

3. A compound of claim 1 wherein Y is an alkyl group having from 1 to 4 carbon atoms.

4. A compound of claim 1 wherein $R_8$ is a straight or branched chain alkyl group having from 1 to 4 carbon atoms.

5. A compound of claim 1 wherein $R_8$ is benzyl.

6. A compound of claim 1 wherein in formula (III) n is 1 or 2.

7. A compound of claim 1 wherein $R_{10}$ is a straight or branched chain alkyl group having 1 to 3 carbon atoms.

8. A compound of claim 1 wherein $R_{11}$ is a straight or branched chain alkyl group having 1 to 3 carbon atoms.

9. A process for the preparation of a compound defined by formula (II) of claim 1, said process comprising the steps of converting a steroid having a —CO—CH$_2$OH chain to a mesylate, converting said mesylate to an iodine-containing derivative, reacting said iodine-containing derivative with an amine function of an amino acid whose carboxylic function is protected by an ester group.

10. The process of claim 9 wherein said steroid is selected from the group consisting of hydrocortisone and dexamethasone.

11. The process of claim 9 wherein said steroid is a glucocorticoid steroid.

12. The process of claim 9 wherein said amino acid is selected from the group consisting of cystine, methionine, glutamic acid and pyroglutamic acid.

13. A process for the preparation of a compound defined by formula (III) of claim 1, said process comprising the steps of converting a steroid to a mesylate, and reacting said mesylate with an amino acid having a free thiol group.

14. The process of claim 13 wherein said amino acid is selected from the group consisting of cysteine and homocysteine.

15. A pharmaceutical composition suitable for administration to a patient suffering from inflammation comprising an anti-inflammatorily effective amount of a compound of claim 1, in admixture with a pharmaceutically acceptable excipient.

16. A pharmaceutical composition of claim 15 in a form suitable for cutaneous administration to a patient, wherein said pharamceutically acceptable excipient is a dermatologically acceptable excipient.

17. A pharmaceutical composition of claim 15 in a form suitable for ophthalmic application to a patient, wherein said pharmaceutically acceptable excipient is an ophthalmologically acceptable excipient.

18. A pharmaceutical composition suitable for administration to a patient suffering from inflammation comprising an anti-inflammatorily effective amount of a compound of claim 2, in admixture with a pharmaceutically acceptable excipient.

19. A pharmaceutical composition of claim 18 in a form suitable for cutaneous administration to a patient, wherein said pharmaceutically acceptable excipient is a dermatologically acceptable excipient.

20. A pharmaceutical composition of claim 18 in a form suitable for ophthalmic application to a patient, wherein said pharmaceutically acceptable excipient is an ophthalmologically acceptable excipient.

* * * * *